(12) United States Patent
Zhu et al.

(10) Patent No.: US 6,897,244 B2
(45) Date of Patent: May 24, 2005

(54) DIHYDRONOOTKATONE AND TETRAHYDRONOOTKATONE AS REPELLENTS TO ARTHROPODS

(75) Inventors: Betty C. R. Zhu, Baton Rouge, LA (US); Gregg Henderson, St. Gabriel, LA (US); Roger A. Laine, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 10/189,631

(22) Filed: Jul. 3, 2002

(65) Prior Publication Data

US 2004/0005343 A1 Jan. 8, 2004

(51) Int. Cl.⁷ ........................ A01N 35/04; A01N 35/06
(52) U.S. Cl. ................ 514/691; 424/405; 424/406; 424/DIG. 10; 514/692; 514/919
(58) Field of Search ................ 424/405, 406; 514/691, 692

(56) References Cited

U.S. PATENT DOCUMENTS

| | | |
|---|---|---|
| 3,835,192 A | 9/1974 | Van Der Linde et al. ... 260/586 R |
| 4,921,696 A | 5/1990 | Vander Meer et al. ........ 424/84 |
| 4,933,371 A | 6/1990 | Hink et al. .................. 514/739 |
| 4,937,073 A | 6/1990 | Fujikura et al. .......... 424/195.1 |
| 5,109,022 A | 4/1992 | Jeanne et al. ............... 514/552 |
| 5,227,163 A | 7/1993 | Eini et al. ................ 424/195.1 |
| 5,303,523 A | 4/1994 | Hand et al. .................... 52/101 |
| 5,411,992 A | 5/1995 | Eini et al. ................... 424/731 |
| 5,591,435 A | 1/1997 | Vaccarello-Dunkel et al. ........... 424/195.1 |
| 5,609,879 A | 3/1997 | Myles ........................ 424/410 |
| 5,696,158 A | 12/1997 | Oliver ......................... 514/463 |
| 5,802,779 A | 9/1998 | Hulls et al. .................... 52/101 |

(Continued)

FOREIGN PATENT DOCUMENTS

| | | |
|---|---|---|
| EP | 1 033 076 A1 | 9/2000 |
| WO | 01/28343 A1 | 4/2001 |

OTHER PUBLICATIONS

Andersen, N., "Biogenetic implications of the antipodal sesquiterpenes of vetiver oil," Phytochemistry, vol. 9, pp. 145–151 (1970).

(Continued)

Primary Examiner—Neil S. Levy
(74) Attorney, Agent, or Firm—Bonnie J. Davis; John H. Runnels

(57) ABSTRACT

Two derivatives of nootkatone, tetrahydronootkatone and 1,10-dihydronootkatone, are surprisingly effective as repellents of termites and mosquitos. Tetrahydronootkatone and 1,10-dihydronootkatone were shown to effectively repel termites at concentrations as low as 2 μg/ml and 12.5 μg/ml, respectively. Tetrahydronootkatone was shown to repel mosquitos at a concentration of 5%. Tetrahydronootkatone is an effective repellent of termites either by itself or as an addition to other substrates, including mulches made from wood products or other cellulose-containing material. Tetrahydronootkatone or 1,10-dihydronootkatone can be used to protect construction wood from attack by Formosan subterranean termites, either alone or used in combination with other compounds known to repel termites. It is also believed that these compounds will prove effective in repelling ants, ticks, and cockroaches. These derivatives of nootkatone are non-toxic to humans and other mammals and environmentally safe.

6 Claims, 1 Drawing Sheet

Nootkatone 1,10-dihydronootkatone

Tetrahydronootkatone

U.S. PATENT DOCUMENTS

| | | | | |
|---|---|---|---|---|
| 5,847,226 | A | | 12/1998 | Muller et al. ............... 568/346 |
| 5,874,097 | A | | 2/1999 | Henderson et al. ......... 424/405 |
| 5,977,186 | A | | 11/1999 | Franklin ..................... 514/690 |
| 6,130,253 | A | | 10/2000 | Franklin et al. ............ 514/690 |
| 6,566,562 | B2 | * | 5/2003 | Wohrle et al. .............. 568/817 |
| 6,624,125 | B2 | * | 9/2003 | Trage et al. ................ 510/101 |
| 6,673,756 | B2 | * | 1/2004 | Sonnenberg et al. ........ 510/141 |
| 2002/0055453 | A1 | * | 5/2002 | Eh et al. ......................... 512/8 |
| 2002/0064203 | A1 | * | 5/2002 | Eh et al. ......................... 512/8 |
| 2003/0068295 | A1 | * | 4/2003 | Rohde et al. .............. 424/76.1 |
| 2004/0001891 | A1 | * | 1/2004 | Smith et al. ................ 424/469 |

OTHER PUBLICATIONS

Andersen, N.H. et al., "Prezizaene and the biogenesis of zizaene," Chemistry and Industry, pp. 62–63 (1971).

Chen, J. et al., "Isolation and identification of 2–phenoxyethanol from a ballpoint pen as a trail–following substance of *Coptotermes formosanus* Shiraki and Reticulitermes spp.", J. Entomol. Sci., vol. 33, pp. 97–105 (1998).

Chen, J. et al., "Termites fumigate their nests with naphthalene," Nature, vol. 392, pp. 558–559 (1998).

Erdtman, H. et al., "The Chemistry of the Natural Order Cupressales XVIII: Nootkatone, a new sesquiterpene type hydrocarbon from the heartwood of *Chamaecyparis nootkatensis* (Lamb.) Spach.," Acta Chem. Scand., vol. 11, pp. 1157–1161 (1957).

Erdtman, H. et al., "The Chemistry of the Natural Order Cupressales 46. The structure of nootkatone,"Acta Chem. Scand., vol. 16, pp. 1311–1314 (1962).

Grace, J.K., "Natural resistance of Alaska–cedar, redwood, and teak to Formonsan subterranean termites," Forest Products Journal, vol. 44, pp. 41–45 (1994).

Ibrahim, S.A. et al., "Efficacy of nootkatone, dihydronootkatone, and tetrahydronootkatone on the Formosan subterranean termite (Isoptera: Rhinotermitidae)," to be submitted to Journal of Economic Entomology, 2002.

Isman, M., "Biopesticides based on phytochemicals," Advances in Biopesticide Research, pp. 1–12 (2000).

Isman, M., "Pesticides based on plant essential oils," Pesticide Outlook, vol. 10, pp. 68–72 (1999).

Kaiser, R. et al., "Biogenetically significant components in vetiver oil," Tetrahedron Letters, vol. 20, pp. 2009–2012 (1972).

Lin, Tien–shu et al., "The effects of *Cinnamomum* spp. oils on the control of the termite *Coptotermes formosanus* Shiraki," Taiwan For. Res. Inst. New Series, vol. 10, pp. 459–464 (1995).

Maistrello, D. et al., "Comparative effects of vetiver oil, nootkatone and Disodium Octoborate Tetrahydrate on *Coptotermas formosanus* and its symbiotic fauna," accepted for publication by Pest Management Science, 2002.

Maistrello, L. et al., "Effects of nootkatone and a borate compound on Formosan subterrean termite (Isoptera: Rhinotermitidae) and its symbiont protozoa," J. Entomol. Sci., vol. 36, pp. 229–236 (2001).

Maistrello, L. et al., "Effects of vetiver oil and its constituents on *Coptotermes formosanus* and its symbiotic fauna," poster presentation at XXI International Congress of Entomology, Iguassu Falls, Brazil, Aug. 20–26, 2000.

Maistrello, L. et al., "Efficacy of Vetiver Oil and Nootkatone as Soil Barriers Against Formosan Subterranean Termite (Isoptera: Rhinotermitidae)," J. Econ. Entomol., vol. 96, No. 6, pp. 1532–1537 (2001).

Miyazawa, M. et al., "Insecticidal sesquiterpene from *Alpinia oxyphylla* against *Drosophila melanogaster*," J. Agric. Food Chem., vol. 48, pp. 3639–3641 (2000).

Stevens, K.L. et al., "Odour character and threshold values of nootkatone and related compounds," J. Sci. Food Agric., vol. 21, pp. 590–593 (1970).

Zhu, B. et al., "Evaluation of vetiver oil and seven insect–active essential oils against Formosan subterranean termites," J. Chem. Ecol., vol. 27, pp. 1617–1625 (2001).

Zhu, B. et al., "Nootkatone is a repellent for Formosan subterranean termites (*Coptotermes formosanus*)," Journal of Chemical Ecotogy, vol. 27, pp. 523–531 (2001).

* cited by examiner

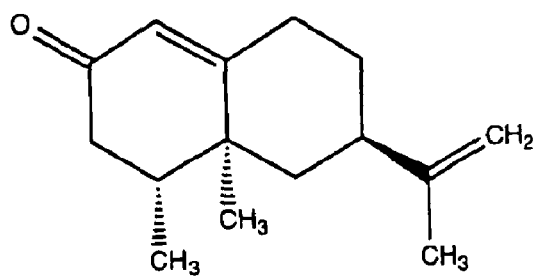
Nootkatone
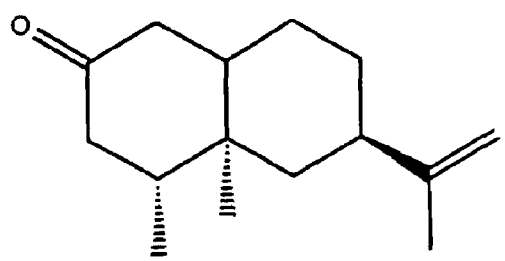
1,10-dihydronootkatone
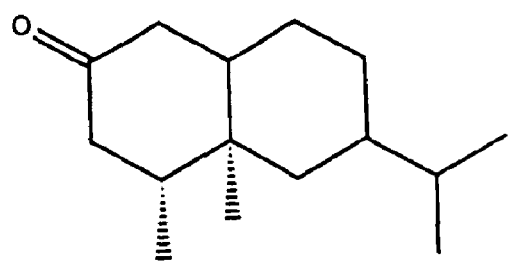
Tetrahydronootkatone
FIGURE

DIHYDRONOOTKATONE AND TETRAHYDRONOOTKATONE AS REPELLENTS TO ARTHROPODS

The development of this invention was partially funded by the Government under a grant from the United States Department of Agriculture, Grant No. USDA/ARS 58-6435-8-084. The Government has certain rights in this invention.

This invention pertains to the use of 1,10-dihydronootkatone and tetrahydronootkatone to repel certain arthropod pests, for example, termites (e.g., *Coptotermes formosanus* Shiraki), mosquitos (e.g., *Aedes vexans*), midges (e.g., *Culicoides* sp.), ticks, ants, and cockroaches.

Various species of insects pose significant economic and health problems for humans. For example, the Formosan subterranean termite, *Coptotermes formosanus* Shiraki, is a major worldwide pest that attacks both living trees and structural wood. Unlike other subterranean termites, the Formosan termite can establish a colony that does not touch the ground.

*Coptotermes formosanus* is native to southeast Asia, but is now also found in Hawaii, along the southeastern Atlantic coast of the United States, and in the Gulf South of the United States. First discovered in the United States by pest control operators in 1965, *C. formosanus* has gradually expanded its geographic domain. The largest single locus of *C. formosanus* in the United States is in south Louisiana, with heavy infestations in Lake Charles and New Orleans. *C. formosanus* may in some cases displace native *Reticulitermes* spp.

Three principal methods have been used in the past to control *Coptotermes*: (1) chemical and physical barriers to prevent termites from attacking wood, (2) wood preservatives and termiticides used to protect infested or susceptible wood, and (3) destruction of a termite colony by excavation of the nest. See, for example, U.S. Pat. Nos. 4,921,696; 5,303,523; 5,609,879; 5,802,779; and 5,874,097. The extensive use of chemical barriers and termiticides have generated public concern over environmental safety.

The search for a new repellent is difficult because studies have shown that termites show unexpected sensitivity and tolerance to certain chemicals, reactions that differ from that of other insects. For example, phenoxyethanol has been shown to be a trail-following substance; and naphthalene, a toxicant for most insects, was found to be used as a fumigant by termites for their nests at concentrations that would kill fire ants. See U.S. Pat. No. 5,874,097; J. Chen et al., "Isolation and identification of 2-phenoxyethanol from a ballpoint pen as a trail-following substance of *Coptotermes formosanus* Shiraki and *Reticulitermes* spp.", J. Entomol. Sci., vol. 33, pp. 97–105 (1998); and J. Chen et al., "Termites fumigate their nests with naphthalene," Nature, vol. 392, pp. 558 (1998).

Natural termite repellent chemicals have been described. The mature leaves of two species of *Cinnamomum, C. osmophloeum* Kaneh. and *C. zeylanicum* B1, have been found to impart termite resistance. The main components of oil extracted from these two species were cinnamic aldehyde and eugenol, respectively, with eugenol exhibiting the greater termite resistance activity. See Tien-shu Lin et al., "The effects of *Cinnamomum* spp. oils on the control of the termite *Coptotermes formosanus* Shiraki," Taiwan For. Res. Inst. New Series, vol. 10, pp. 459–464 (1995). Additionally, the woods of Alaska-cedar, redwood, and teak were found to be resistant to Formosan subterranean termites. Although the termites fed on the woods, it was only to a very limited extent. See J. K. Grace, "Natural resistance of Alaska-cedar, redwood, and teak to Formosan subterranean termites," Forest Products Journal, vol. 44, pp. 41–45 (1994).

Mosquitos are another major pest, particularly in warmer climates. Many diseases can be transmitted through the bite of a mosquito. There is a need for effective repellents against mosquitos, particularly repellents that could be applied directly to the skin.

Ants are another major worldwide pest. For example, leaf-cutting ants defoliate citrus trees. In the southern United States, red imported fire ants, *Solenopsis invicta* Buren, pose problems for growing crops, young trees, wildlife, pets, electrical equipment, etc. Fire ants also pose a health threat to people. Many people are stung multiple times by fire ants, and these multiple stings can severely affect those who are allergic to ant stings, especially the very young or the very old. Fire ants belong to the Class Hexapoda, Order Hymenoptera.

The primary control for ants currently involves the use of insecticides. However, insecticides offer only temporary relief due to a high reproductive capacity, an efficient foraging behavior, and the ecological adaptability of ants. Moreover, many insecticides pose a threat to beneficial animals, including birds and mammals. There is a need for a compound that is relatively non-toxic to birds and mammals, but is still effective as a repellent or toxicant to ants.

The search for new repellents for arthropods is difficult because studies have shown that arthropods, particularly insects, display widely differing sensitivities to different chemicals, including many insecticides. For example, although some essential oils have been shown to be toxic or repellent to some kinds of insects, the toxicity of an essential oil to a particular insect pest species, and selectivity among species have been described as idiosyncratic. See M. Isman, "Pesticides based on plant essential oils," Pesticide Outlook, vol. 10, pp. 68–72 (1999). For example, acyl derivatives of phenols from essential oils have been found to be more active against fly eggs than are the parent phenols, but less effective when applied topically to adult flies. Ether derivatives of monoterpenes from essential oils were found to be more effective against some, but not all insect species assayed. See Isman, 1999.

Naphthalene, a toxicant for most insects, was found to be used by termites as a beneficial fumigant for their nests at concentrations that kill another group of insects, the fire ants. See U.S. Pat. No. 5,874,097; and J. Chen et al., "Termites fumigate their nests with naphthalene," Nature, vol. 392, pp. 558 (1998). Moreover, unlike many herbivorous insects, omnivorous insects (e.g., fire ants) may not be affected by many chemicals evolved by plants for protection from insect pests. See M. Isman, "Biopesticides based on phytochemicals," Advances in Biopesticide Research, (2000).

The differences in sensitivity to specific chemicals among major insect groups may reflect that these groups have diverged from one another many millions of years ago. The oldest insect fossil known has been dated to be about 400 million years old. One of the most ancient insect groups is the cockroaches, which appeared in the fossil record about 300 million years ago. Termites appeared about 250 million years ago. The hymenopterans, including ants, bees and wasps, appeared about 200 million years ago. Fleas and the dipterans (flies and mosquitos) appeared about 240 million years ago.

Ticks, although belonging to the same phylum as insects, Arthropoda, are more closely related to spiders and mites. Ticks belong to the Class Arachnida and Order Acari. Ticks feed on the blood of mammals, birds, and reptiles. Ticks usually are found on the ends of grass blades until attracted by a host. Host attractants include chemical attractants, e.g., lactic acid and carbon dioxide, and physical movement. Ticks cause several diseases in humans, including spotted fever, relapsing fever, tularemia, Lyme disease, and Texas cattle fever. One of the tick species known to transmit Lyme disease is *Ixodes scapularis*.

Cockroaches are one of the oldest groups of insects, having existed for approximately 350 million years. Cockroaches belong to the Class Hexapoda and Order Blatteria. They have an incomplete metamorphosis, in which the young cockroaches look and behave similarly to the adults. Cockroaches are omnivores and will eat almost any human food. German cockroaches, *Blattella germanica*, are the most problematic species of cockroaches in the U.S. Cockroaches are a major cause of asthma in the U.S. and also carry many disease organisms in and on their bodies.

Biting midges (*Culicoides* sp.) of the family Ceratopogonidae are the smallest of the blood sucking insects and are common pests in the United States, where they are commonly called "punkies," "sand flies," and "no-see-ums."

Nootkatone, or 4,4a,5,6,7,8-hexahydro-6-isopropenyl-4,4a-dimethyl-2(3H)-naphthalone, is a mildly pungent sesquiterpene ketone found in the oil of Alaska yellow cedar (*Chamaecyparis nootkatensis*) and in a great number of citrus oils, especially oil from grapefruit (*Citrus pavadisi*). Nootkatone is widely used in the perfumery and flavor industries being essentially non-toxic to humans. See U.S. Pat. Nos. 3,835,192 and 5,847,226; H. Erdtman et al., "The Chemistry of the Natural Order Cupressales XVIII: Nootkatone, a new sesquiterpene type hydrocarbon from the heartwood of *Chamaecyparis nootkatensis* (Lamb.) Spach.," Acta Chem. Scand., vol. 11, pp. 1157 (1957); and H. Erdtman et al., "The Chemistry of the Natural Order Cupressales 46. The structure of nootkatone," Acta Chem. Scand., vol. 16, pp. 1311 (1962). Nootkatone has also been identified as a minor component of vetiver oil. See U.S. Pat. No. 4,937,073; and N. H. Andersen et al., "Prezizaene and the biogenesis of zizaene," Chemistry and Industry, pp. 62–63 (1971); N. Andersen, "Biogenetic implications of the antipodal sesquiterpenes of vetiver oil," Phytochemistry, vol. 9, pp. 145–151 (1970); and R. Kaiser et al., "Biogenetically significant components in vetiver oil," Tetrahedron Letters, vol. 20, pp. 2009–2012 (1972). The structure of nootkatone is shown below.

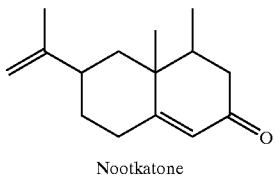

Nootkatone

Nootkatone and epinootkatol, as extracts of the Japanese fruit *Alpinia oxyphylla*, were recently identified as having insecticidal activity against the larval and adult stages of *Drosophila melanogaster*. See M. Miyazawa et al., "Insecticidal sesquiterpene from *Alpinia oxyphylla* against *Drosophila melanogaster*," J. Agric. Food Chem., vol. 48, pp. 3639–3641 (2000). Flies belong to the Class Hexapoda and Order Diptera.

Nootkatone and several related compounds, including dihydronootkatone and tetrahydronootkatone, are known to have somewhat different odor and threshold characteristics. See K. L. Stevens et al., "Odour character and threshold values of nootkatone and related compounds," J. Sci. Food Agric., vol.21, pp.590–593 (1970). In particular, both tetrahydronootkatone and 1,10-dihydronootkatone were rated with less desirable grapefruit aroma than nootkatone or the other tested related compounds (e.g., isonootkatone and 11,12-dihydronootkatone).

European Patent Application No. EP 1033076 A1 discloses the use of an aerosol containing nootkatone, valencene or a mixture to repel mosquitos of the genera *Culex* and *Aedes*. Mosquitos belong to the arthropod Class Hexapoda and the Order Diptera.

U.S. Pat. Nos. 6,130,253 and 5,977,186 disclose a terpene-based pesticide for killing terrestrial arthropods, including lice, mites, and ants, wherein the terpenes discussed include limnoene, beta-ionone, linalool, geraniol, eugenol, carvone, myrcene, and citral.

U.S. Pat. No. 5,696,158 discloses a repellent composition for lice containing piperonal as a main ingredient.

U.S. Pat. No. 5,591,435 discloses a composition as an insecticide or as an insect behaviorally active composition comprising compounds from aromatic plants, including geranium, balsam root, sage brush, African mint, and horse mint.

U.S. Pat. Nos. 5,411,992 and 5,227,163 disclose lice-repellent compositions comprising terpenoids, especially terpenoid-alcohols, terpenoid-esters, and some aldehydes and ketones of terpenes, excluding the terpene linalool.

U.S. Pat. No. 5,109,022 discloses insect repelling substances, including methyl myristate, methyl palmitate, butyl palmitate or combination thereof.

U.S. Pat. No. 4,933,371 discloses the use of linalool as a pesticide against ticks and fleas.

Certain extracts of vetiver oil derived from vetiver grass, *Vetiveria zizanoides*, including nootkatone, α-cedrene, zizanol and bicyclovetivenol, were found to be effective repellents and toxicants of termites. Nootkatone was found to be a component of one of the termite-repelling extracts from vetiver oil. See B. Zhu et al., "Nootkatone is a repellent for Formosan subterranean termites (*Coptotermes formosanus*)," Journal of Chemical Ecology, vol. 27, pp. 523–531 (2001); L. Maistrello et al., "Effects of nootkatone and a borate compound on Formosan subterranean termite (Isoptera: Rhinotermitidae) and its symbiont protozoa," J. Entomol. Sci., vol. 36, pp. 229–236 (2001); L. Maistrello et al., "Efficacy of vetiver oil and nootkatone as soil barriers against Formosan Subterranean termite (Isoptera: Rhinotermitidae)," J. Econ. Entomol., vol.94, pp.1532–1537 (2001); B. Zhu et al., "Evaluation of vetiver oil and seven insect-active essential oils against Formosan subterranean termites," J. Chem. Ecol., vol. 27, pp. 1617–1625 (2001); and L. Maistrello et al., "Effects of vetiver oil and its constituents on *Coptotermes formosanus* and its symbiotic fauna," poster presentation at XXI International Congress of Entomology, Iguassu Falls, Brazil, Aug. 20–26, 2000; and the complete text of the U.S. provisional application, Ser. No.60/160,251, filed Oct. 19, 1999; and of the international application PCT/US00/29006, filed Oct. 18, 2000; published as WO 01/28343.

We have discovered that two derivatives of nootkatone, both tetrahydronootkatone and 1,10-dihydronootkatone, are surprisingly effective as repellents of termites and mosquitos. Tetrahydronootkatone and 1,10-dihydronootkatone were shown to effectively repel termites at concentrations that were 50 and 8 times, respectively, lower that the effective concentration of nootkatone. Tetrahydronootkatone was shown to repel mosquitos and biting midges at a concentration of 5%. Both tetrahydronootkatone and 1,10- dihydronootkatone are effective repellents of termites either alone or as additions to other substrates, including mulches made from non-cellulose and cellulose materials. Tetrahydronootkatone or 1,10-dihydronootkatone can be used to protect construction wood from attack by Formosan subterranean termites, either alone or used in combination with other compounds known to repel termites. It is also believed that these compounds will prove effective in repelling ants, ticks, and cockroaches. These derivatives of nootkatone are non-toxic to humans and other mammals and environmentally safe; they are currently sold as flavorings and as ingredients for fragrances.

BRIEF DESCRIPTION OF THE DRAWINGS

The FIGURE illustrates the chemical structures of nootkatone, 1,10-dihydronootkatone, and tetrahydronootkatone.

Commercially available nootkatone, 1,10-dihydronootkatone, and tetrahydronootkatone were used to test for effectiveness as a repellent to termites, mosquitos, and midges. These two derivatives of nootkatone (1,10-dihydronootkatone and tetrahydronootkatone) were found to be effective repellents at much lower concentrations than nootkatone itself. The structures of nootkatone, 1,10-dihydronootkatone, and tetrahydronootkatone are shown in the FIGURE. Additionally, we believe that both tetrahydronootkatone and 1,10-dihydronootkatone will be effective repellents of ants, ticks, and cockroaches. These derivatives can also be added to currently known repellents and toxicants to increase the effectiveness against the arthropod pests. Examples of such known repellents and toxicants include the following: nootkatone, α-cedrene, zizanol, bicyclovetivenol, pyrethroids, methyl myristate, methyl palmitate, butyl palmitate, octyl stearate, octyl palmitate, plus many more.

EXAMPLE 1
Purification of Chemicals and Source of Termites:

Purification of Dihydronootkatone and Tetrahydronootkatone.

Nootkatone (4,4a,5,6,7,8-hexahydro-6-isopropenyl-4,4a-dimethyl-2(3H)-naphthalenone; >97% crystalline) was purchased from a commercial source (Lancaster Synthesis Inc., Windham, N.H.). Both 1,10-dihydronootkatone (1,4,4a,5,6,7,8,10-octahydro-6-isopropenyl-4,4a-dimethyl-2(1H)-naphthalenone; >85% crystalline) and tetrahydronootkatone (1,4,4a,5,6,7,8,10-octahydro-6-isopropl-4,4a-dimethyl-2(1H)-naphthalenone; >85% crystalline) were commercially available (Subcon Products, Inc., Totowa, N.J.). Prior to conducting the bioassays, 1,10-dihydronootkatone and tetrahydronootkatone were further purified by the following procedure: A 1 g sample of either 1,10-dihydronootkatone or tetrahydronootkatone was dissolved in 5 ml of 95% ethyl alcohol, and then mixed with 5 g of silica gel. The mixed sample was air-dried for 15 min, and then applied to the bottom of a glass column (2 cm×30 cm). The glass column was filled with silica gel, and then developed with chloroform in an ascending run. The silica gel was removed from the column in 2.5 cm sections as the chloroform reached the top. Once the chloroform reached the top of the column, each 2.5 cm section of silica gel was collected in a flask for extraction with 40 ml ethyl alcohol. A sample from each fraction was checked on analytical thin layer chromatography (TLC). The TLC silica plate was developed with $CHCl_3$, and the color was visualized by spreading with 50% $H_2SO_4$ and heating to 120° C. The purified 1,10-dihydronootkatone and tetrahydronootkatone (both >97%) were confirmed with gas chromatography-mass spectroscopy (GC-MS) (data not shown).

Termite Source.

A carton nest (colony A) of Formosan subterranean termites was collected in Algiers, Louisiana in November 1997, and held in 250-liter cans. The cans were filled with pine as a food source, and kept at a temperature range of 24–26° C. Moistened corrugated cardboard rolls were used to retrieve termites from the cans. Once the termites migrated to the cardboard rolls, they were gently knocked from the cardboard rolls into clean rectangular plastic trays (40 cm×50 cm). Retrieved termites were isolated from debris by allowing them to cling to sheets of moistened paper towels. The average weight of each termite was 1.21 mg.

EXAMPLE 2
Bio-Activity of Nootkatone, Dihydronootkatone and Tetrahydronootkatone Against Termites To test for effectiveness of nootkatone, 1,10-dihydronootkatone and tetrahydronootkatone in repelling termites, a bioassay was conducted using Petri dishes (5 cm diameter and 1 cm height). To ensure adequate moisture for the termites, 1 ml of a hot agar solution (1.5% in $H_2O$) was spread on the bottom of the Petri dish. After the agar cooled, sand that was treated as described below was spread on the bottom of the Petri dish. For the treated sand, purified 1,10-dihydronootkatone or tetrahydronootkatone were dissolved in 2 ml ethanol, and then diluted to achieve final concentrations of 1, 2, 5, 12.5, 25, 50, and 100 $\mu$g/g sand. The solution was mixed with 1 g sand that had been autoclaved and cooled. The control sand was autoclaved sand with only 200 $\mu$l ethanol added. One half of the surfaces in the Petri dishes were covered with 1 g treated sand, and the other half with 1 g untreated sand.

The prepared Petri dishes were then used to evaluate the repelling activity against Formosan subterranean termites. Ten worker termites were added to each Petri dish, and the dishes were covered to eliminate light. Five replicate dishes were tested for each concentration and for the control. Termite position was recorded every 15 min during the first hour of testing by counting the number of termites observed on untreated sand. After the first hour, termite position was recorded each hour for 3 hr.

Differences between the percent of termites on untreated sand and an expected value were statistically analyzed by a Chi-Square analysis, using an expected value of 50% and a significance level of $p \leq 0.05$. The results are presented in Table 1. In Table 1, "/" indicates that no test was conducted; "−" indicates the test was not significantly different from the expected value; and "+" indicates the test was significantly different from the expected value.

TABLE 1

| Time (hour) | Concentration ($\mu$g/dish) | | | | | | |
|---|---|---|---|---|---|---|---|
| | 1 | 2 | 5 | 12.5 | 25 | 50 | 100 |
| A. Nootkatone | | | | | | | |
| 0.25 | / | − | − | − | − | + | + |
| 0.5 | / | − | − | − | − | − | + |
| 0.75 | / | − | − | − | − | − | + |
| 1 | / | − | − | − | − | + | + |
| 2 | / | − | − | − | − | − | + |
| 3 | / | − | − | − | − | − | + |

TABLE 1-continued

| Time (hour) | Concentration (μg/dish) | | | | | | |
|---|---|---|---|---|---|---|---|
| | 1 | 2 | 5 | 12.5 | 25 | 50 | 100 |
| B. Dihydronootkatone | | | | | | | |
| 0.25 | / | − | − | + | − | + | + |
| 0.5 | / | − | − | + | + | + | + |
| 0.75 | / | − | − | + | + | + | + |
| 1 | / | − | − | + | + | + | + |
| 2 | / | − | − | + | + | + | + |
| 3 | / | − | − | + | + | + | + |
| C. Tetrahydronootkatone | | | | | | | |
| 0.25 | − | + | − | + | − | + | + |
| 0.5 | − | + | + | + | + | + | + |
| 0.75 | − | + | + | + | + | + | + |
| 1 | − | + | + | + | + | + | + |
| 2 | − | + | + | + | + | + | + |
| 3 | − | + | + | + | + | + | + |

As shown in Table 1, a concentration of 100 μg/dish nootkatone was required before the termite distribution indicated a significant effect of the treated sand for time periods greater than 1 hr. In contrast, a concentration of 12.5 μg 1,10-dihydronootkatone was effective for time periods up to 3 hr; and 2 μg tetrahydronootkatone was effective for up to 3 hr. In this analysis, 1,10-dihydronootkatone and tetrahydronootkatone were effective as termite repellents at much lower concentrations than nootkatone by factors of 8 and 50, respectively.

EXAMPLE 3
Bio-Activity of Tetrahydronootkatone Against Mosquitos

To test the repellence of tetrahydronootkatone on mosquitos, tetrahydronootkatone was dissolved in 70% isopropyl alcohol to a final concentration of 5%. This solution was used to topically apply to the arms of two male volunteers. Each volunteer cleaned each arm thoroughly with soap and water, and then wiped down each arm with 70% isopropyl alcohol. The right arm of each volunteer was treated with 5 ml of the 5% tetrahydronootkatone solution. The left arm served as a control. To test for mosquito repellence, each arm of a single volunteer was placed into a cage of freshly collected mosquitoes, about 100 mosquitos per cage. The mosquitoes were salt marsh mosquitoes, *Aedes vexans*. After 2 min, the number of mosquito bites on each arm were counted. Tests were run at 5 min, 1 hr, 2 hr, and 3 hr after the initial application of tetrahydronootkatone. The results are presented in Table 2.

TABLE 2

Effect of Treatment with Tetrahydronootkatone on Number of Mosquito Bites in a 2 min Period.

| | 5 min | 1 hr | 2 hr | 3 hr |
|---|---|---|---|---|
| Volunteer 1 | | | | |
| Tetra Arm | 0 | 0 | 0 | 0 |
| Control Arm | 5 | 4 | 4 | 6 |
| Volunteer 2 | | | | |
| Tetra Arm | 0 | 0 | 0 | 2 |
| Control Arm | 3 | 5 | 0 | 3 |

Although the numbers are low, the results in Table 2 indicate that a 5% solution of tetrahydronootkatone is an effective mosquito repellent for time periods up to 3 hr after the initial application. These compounds can be used for topical application either singly or in combination with one or more additional compounds selected from the group consisting of 1,10-dihydronootkatone, tetrahydronootkatone, nootkatone, zizanol, bicyclovetivenol, and α-cedrene. These compounds can also be used in combination with other known contact repellents, e.g., octyl-palmitate and octyl-stearate.

EXAMPLE 4
Bio-Activity of Tetrahydronootkatone Against Biting Midges

To test the repellence of tetrahydronootkatone on biting midges (family Ceratopogonidae, genus *Culicoides*), tetrahydronootkatone was dissolved in 70% isopropyl alcohol to a final concentration of 5%. This solution was used to topically apply to the faces of two adult male volunteers. Four other adult males did not apply this solution. The six males went into a southern Louisiana marsh, an area known for biting midges. The two males with the tetrahydronootkatone solution reported fewer problems with biting midges, while the other four males reported many midges swarming around their faces.

Although the numbers are low, these results indicate that a 5% solution of tetrahydronootkatone is an effective repellent for biting midges. These compounds can be used for topical application either singly or in combination with one or more additional compounds selected from the group consisting of 1,10-dihydronootkatone, tetrahydronootkatone, nootkatone, zizanol, bicyclovetivenol, and α-cedrene. These compounds can also be used in combination with other known contact repellents, e.g., octyl-palmitate and octyl-stearate.

Thus the results indicated above for both termites, mosquitos, and biting midges indicate that these three arthropod species respond to the two derivatives of nootkatone tested, 1,10-dihydronootkatone and tetrahydronootkatone. We believe that 1,10-dihydronootkatone and tetrahydronootkatone will also be effective repellents to ants, ticks, and cockroaches.

We have previously discovered that nootkatone was a significant repellent and toxicant of ants and ticks, and a repellent to cockroaches. We also demonstrated that fleas were not affected by nootkatone. See U.S. patent application, Ser. No. 09/932,555, filed Aug. 17, 2001.

Both 1,10-dihydronootkatone and tetrahydronootkatone can be added to materials to effectively repel several arthropod pests. The addition can be by treating the material with a solution or with a vapor or any other method that would incorporate the compounds either into or onto the material. Examples of such materials include wood, paper, cardboard, canvass, leather, feathers, and synthetic polymers. Such materials can be used as building materials, e.g., for floors, walls, or cabinets, or for tents, sleeping bags, or clothes. In addition, these compounds can be used in compositions for topical application to humans to repel mosquitos, midges, and ticks. Examples of topical application include addition of these compounds to shampoos, soaps, lotions or sprays used for sun screen and insect repellents.

Nootkatone is non-toxic to humans and other mammals and is environmentally safe. It is also believed that these derivatives of nootkatone are non-toxic to humans.

EXAMPLE 5
Bio-Activity of Dihydronootkatone and Tetrahydronootkatone Against Ants The fire ant bio-activity of 1,10-dihydronootkatone and tetrahydronootkatone will be tested using five cm diameter Petri dishes with lids. Two ml of hot agar solution (1.5 gm/100 ml ddH$_2$O) will be spread evenly in the bottom of each dish and allowed to cool. The agar solution will provide moisture for the fire ants and hold the sand in place. The sand will be autoclaved for 30 min before adding either ethanol alone or ethanol with sample. Then the sand will be dried in an oven. For three dishes, one half of the bottom of each dish will be covered with 1.5 gm sand previously mixed with a total of 100 μg (or other amounts) either 1,10-dihydronootkatone or tetrahydronootkatone per dish, dissolved in ethanol, and the other half with 1.5 gm untreated sand (only ethanol). The sand will completely cover the agar, but will not be thick enough to conceal the fire ants. Three dishes will be prepared as controls with only untreated sand in each side.

Imported red fire ants, *Solenopsis invicta*, will be collected the day before beginning the experiment from Louisiana colonies. Ten fire ant workers will be added to each dish, and the dishes covered to eliminate light.

The fire ant distribution in each dish, measured by counting the number of fire ants on the untreated half of the dish, will be examined each hour for up to 8 hr. When 70% or more of the fire ants (in at least three replicates) are observed on the untreated sand, the sample will be considered to have activity as a repellent. Also, the number of fire ants that are normal, ataxic, moribund or dead will be recorded.

It is expected that 1,10-dihydronootkatone and tetrahydronootkatone will be effective repellents for fire ants, at least in the 2–3 hr time frame.

EXAMPLE 6
Bio-Activity of Dihydronootkatone and Tetrahydronootkatone Against Ticks To test the effectiveness of 1,10-dihydronootkatone and tetrahydronootkatone against ticks, ticks (*Ixodes scapularis*) will be collected from Idlewild, La. 1,10-dihydronootkatone and tetrahydronootkatone efficacy will be tested relative to a known repellent, N,N-diethyl-m-toluamide ("Deet"). REPEL®, which contains 27.55% Deet, will be purchased locally from a retail garden store.

A bioassay will be conducted using Petri dishes (5 cm diameter and 1 cm height). To ensure adequate moisture for the ticks, 1 ml of a hot agar solution (1.5% in H$_2$O) will be spread evenly on the inside surfaces of the Petri dish, including the top, bottom, and edges. After the agar cools, sand that was treated as described below will be spread evenly on the inside surfaces of the Petri dish. The sand will be held in place by the agar.

For the treated sand, either 2 mg sample (either 1,10-dihydronootkatone or tetrahydronootkatone nootkatone) or 100 mg REPEL® will be dissolved in 2 ml ethanol, and then 200 μl of the solution will be mixed with 2 g sand that had been autoclaved and cooled. The control will be autoclaved sand with 200 μl ethanol only added. One half of the surfaces in the Petri dishes will be covered with 2 g treated sand, and the other half with 2 g untreated sand. In the sample-treated Petri dishes, the final concentration will be 200 μg/dish; while in the Deet treated Petri dishes, the final concentration will be 2.75 mg/dish. Control Petri dishes will be prepared by covering all sides with untreated sand.

One tick will be added to each Petri dish, and the top replaced. The number of replicates will be about 8 for controls, samples, and Deet. The Petri dishes will be checked at 15 min, 30 min, 1 hr, 2 hr, 3 hr, 4 hr, 5 hr, 6 hr, 68 hr, and 90 hr. Repellent activity will be noted it the tick is found on the untreated side of the Petri dish. The ticks in the control Petri dishes are expected to be randomly distributed on the left and right sides.

It is expected that 1,10-dihydronootkatone and tetrahydronootkatone will be effective repellents and toxicants against ticks. It is also expected that both 1,10-dihydronootkatone and tetrahydronootkatone will maintain repellent activity longer than Deet, and will be stronger toxicants than Deet.

EXAMPLE 7
Bio-Activity of Dihydronootkatone and Tetrahydronootkatone Against Cockroaches To test the efficacy of 1,10-dihydronootkatone and tetrahydronootkatone against cockroaches, German cockroaches (*Blattella germanica*) will be collected locally on the same day that the bioassay will be run.

For the bioassay, Petri dishes (10 cm diameter×1 cm) will be used. The Petri dishes will be prepared by lining one half of the top and one half of the bottom with a half circle of filter paper (125 mm), and lining the other half with a second half circle of filter paper. For the treated Petri dishes, 50 mg sample (either 1,10-dihydronootkatone or tetrahydronootkatone) and 300 mg REPEL® will be dissolved in 2.0 ml ethanol. To each Petri dish will be added either ethanol only, 30 mg Deet, 1 mg sample, or 10 mg sample. Ten replicate Petri dishes will be used for each of the treatments. The ethanol solution will be added to the filter paper on the top and bottom and dried for 10 min. One cockroach will be added to each Petri dish. The length of the cockroaches will be approximately the same. The dishes will then be observed at 15 min, 30 min, 1 hr, 2 hr, 3 hr, 4 hr, 5hr, 24 hr, 48 hr, and 120 hr.

It is expected that Deet will have no significant repellent activity against cockroaches. In contrast, it is expected that both 1,10-dihydronootkatone and tetrahydronootkatone will be strong repellents, and that the repellence will be long lasting.

In the specification and the claims, an "effective amount" of 1,10-dihydronootkatone or tetrahydronootkatone is defined to be an amount that, when topically applied to skin or applied to a substrate or other material, causes significant repellence or toxicity to an arthropod as compared to an otherwise identical environment without the addition of 1,10-dihydronootkatone or tetrahydronootkatone.

In the claims, the "outer surface of an animal" is defined to include scales, skin, fur, or feathers of a vertebrate, or clothes as might be worn by the animal, e.g., a human.

The complete disclosures of all references cited in this specification are hereby incorporated by reference. Also incorporated by reference are the complete disclosures of the following unpublished manuscripts: D. Maistrello et al. "Comparative effects of vetiver oil, nootkatone and disodium octoborate tetrahydrate on *Coptotermes formosanus* and its symbiotic fauna," accepted for publication by Pest Management Science; S. A. Ibrahim et al., "Efficacy of nootkatone, dihydronootkatone, and tetrahydronootkatone on the Formosan subterranean termite (Isoptera: Rhinotermitidae)," to be submitted to Journal of Economic Entomology; and the complete text of U.S. patent application Ser. No. 09/932,555, filed Aug. 17, 2001. In the event of an otherwise irreconcilable conflict, however, the present specification shall control.

We claim:
1. A method for protecting an animal from arthropods, comprising topically applying to the outer surface of the animal a composition, said composition comprising:
  (a) an effective amount of a compound selected from the group consisting of 1,10-dihydronootkatone and tetrahydronootkatone, and

(b) a pharmaceutically accepted carrier;
wherein the topical application of said composition to an outer surface of an animal repels or kills one or more arthropods selected from the group consisting of mosquitos, midges, ants and ticks substantially more than does an otherwise identical composition that lacks the compound.

2. A method as in claim 1, wherein the ants are fire ants.

3. A method as in claim 1, wherein said compound is 1,10-dihydronootkatone.

4. A method as in claim 1, wherein said compound is tetrahydronootkatone.

5. A method as in claim 1, said composition additionally comprising one or more additional, different compounds selected from the group consisting of 1,10-dihydronootkatone, tetrahydronootkatone, nootkatone, zizanol, bicyclovetivenol, α-cedrene, octyl-palmitate, octyl-stearate, methyl palmitate, and methyl stearate.

6. A method as in claim 1, said composition additionaily comprising one or more additional, different arthropod repellents and toxicants.

* * * * *